United States Patent [19]

Austin et al.

[11] Patent Number: 5,617,869
[45] Date of Patent: Apr. 8, 1997

[54] DEVICE AND METHOD FOR LOCATING FLOW BLOCKAGE IN A THREE-DIMENSIONAL OBJECT

[75] Inventors: Stephen A. Austin, Amston; Andrew J. Hull, New London; Norman L. Owsley, Gales Ferry; Mark S. Peloquin, New London, all of Conn.

[73] Assignee: The United States of America as represented by the Secretary of the Navy, Washington, D.C.

[21] Appl. No.: 491,385

[22] Filed: Jun. 16, 1995

[51] Int. Cl.⁶ .................................................. A61B 5/02
[52] U.S. Cl. ....................... 128/691; 128/672; 128/675; 128/677; 128/687
[58] Field of Search .............................. 128/672, 675, 128/677, 687, 691

[56] References Cited

U.S. PATENT DOCUMENTS 4,802,488  2/1989  Eckerle .................................. 128/672
5,005,581  4/1991  Honeyager ........................ 128/672 X
5,396,895  3/1995  Takashima et al. ............... 128/672 X

*Primary Examiner*—Lee S. Cohen
*Assistant Examiner*—Stephen D. Huang
*Attorney, Agent, or Firm*—Michael J. McGowan; James M. Kasischke; Prithvi C. Lall

[57] ABSTRACT

A method and apparatus for locating artery stenoses in blood vessels includes providing an array of sensors on skin surface to acquire data for detecting, locating and analyzing energy emissions in three-dimensional objects. The array detects momentum transfer that exists in the object in the form of wave energy, and the detection is designed to occur on the surface of the object, thereby providing a non-intrusive method for locating artery stenoses, with localization of the artery stenoses being achieved through array signal processing by information detected on the surface of the skin with the plurality or array of sensors.

18 Claims, 1 Drawing Sheet

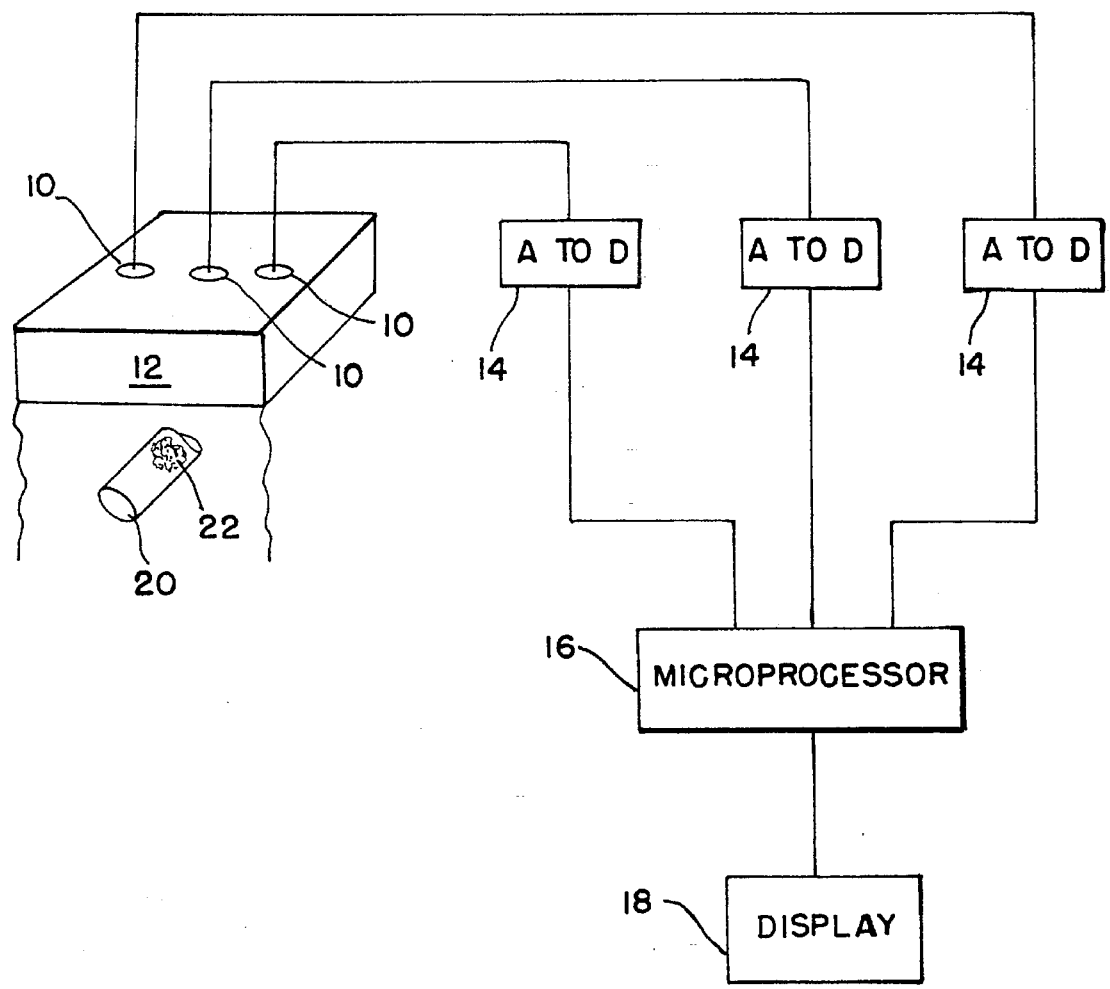

5,617,869

DEVICE AND METHOD FOR LOCATING FLOW BLOCKAGE IN A THREE-DIMENSIONAL OBJECT

STATEMENT OF GOVERNMENT INTEREST

The invention described herein may be manufactured and used by, or for, the government of the United Statement of America for governmental purposes without the payment of any royalties thereon or therefor.

BACKGROUND OF THE INVENTION (1) Field of the Invention

The present invention generally relates to a method and apparatus for locating artery stenoses in blood vessels. More particularly, the present invention is directed to the use of array sensor technology to determine the location of artery stenoses in animals and human beings.

(2) Description of Prior Art

There have previously been known several methods in the art for detecting artery disease, including the most traditional method, which relies upon the ability of a practitioner to detect the existence of artery stenoses with a stethoscope. Other recently known methods include the use of microphones, amplifiers, and recording oscillographs.

However, none of the known methods accurately and efficiently determine the location of the blockage within the artery, nor do the known methods provide for analysis of a detected and localized artery stenosis in humans and animals. Accordingly, the currently known methods are not completely effective for early stage diagnosis of artery disease. Further, the known methods for locating artery stenoses in blood vessels are unable to effectively eliminate background noises including heartbeat, pulse and breathing, which will interfere with the detection of the blockage in the blood vessel.

One specifically known method and apparatus for the detection and recordation of high frequency sound in the cardiovascular system is found in U.S. Pat. No. 3,762,397 to Cage. This apparatus, however, utilizes only a single microphone placed on the surface of the skin instead of an array of motion sensors, and is therefore unable to effectively increase the signal to noise ratio of the signals emitted from the noise source.

Another method which utilizes a microphone for detection of sound is disclosed in U.S. Pat. No. 3,773,033 to Robard et al. In addition to the microphone, an arterial vibration sensor is utilized. Neither of the microphone nor the sensor, however, is utilized in an array.

U.S. Pat. No. 4,989,611 to Zanetti et al. discloses a cardiac compression wave measuring system and method. Although a sensor is utilized, it is only known to provide a single sensor as opposed to an array of sensors. Further, only compression waves are detected and measured whereas the invention described in accordance with the present application utilizes an array of sensors which measure all wave energy, including but not limited to compression waves.

Another non-invasive diagnostic system for coronary artery disease is disclosed in U.S. Pat. No. 5,109,863 to Semmlow et al. and utilizes an acoustic transducer. The sensor, however, is a single sensor and is not intended to function as an array.

Each of U.S. Pat. Nos. 5,170,796 to Kobayashi and U.S. Pat. No. 5,293,874 to Takahashi et al. are directed to the detection and measurement of pulse waves. The focus of these patents is on pulse waves and does not include detection of all wave energy in the human body. With regard to Kobayashi, only pressure sensors are used to the exclusion of motion and strain sensors, as are disclosed in the instant application. Additionally, Kobayashi requires that each pressure sensing element is smaller than the lumen in the blood vessel and further that the pressure sensing elements cross over the radial artery substantially perpendicular to the direction of extension of the artery. Such a requirement presumes exact knowledge of the location of the artery as well as the orientation of the sensors with respect to the artery, thus excluding the possibility of detection at some part of the body including a blood vessel which is not near the skin surface. Further, the sensors of Kobayashi are plural in number in order to generate a scan sequence in order to provide a reference distribution whereas the present invention utilizes the array to improve the signal to background noise ratio to detect desired signals.

In Takahashi, the sensors for pulse wave detection are not used as an array but are instead positioned at upstream and downstream sides of a blood flow for measuring a transmission velocity of a pulse wave.

SUMMARY OF THE INVENTION

Therefore, it is one object of the present invention to provide a method and apparatus for locating artery stenoses in blood vessels.

Another object of the present invention is to provide a method and apparatus for locating artery stenoses in blood vessels utilizing array sensor technology to determine the location and size of the artery stenoses.

Still another object of the present invention is to utilize only non-invasive sensors which will detect wave motion emitted by occlusions in partially blocked arteries, the wave motion originating at the occlusion and being detected on the surface of the skin by the array of sensors.

In accordance with one aspect of this invention, there is provided a method for locating artery stenoses in blood vessels. The method includes positioning an array of sensors on a surface of the skin. Waveform energy is detected on the skin surface by the array of sensors followed by identifying a change in waveform energy on the surface of the skin by at least one sensor in the array of sensors. Next, at least spectral, directional, and intensity characteristics of waveform energy sensed by each sensor in the array of sensors is determined, and the stenoses is located on the basis of the step of determining.

In accordance with another aspect of this invention, there is provided an apparatus or device for detecting acoustic emissions in a dimensional object. The apparatus includes a sensor array positioned on the surface of the object, each sensor in the sensor array detecting waveform fluctuations on the surface of the object. Means are provided for converting the detected waveform fluctuation from analog to digital, and a micro-processor unit is responsive to the converted digital waveform energies, for reducing background noise and identifying variations in waveform energy at the surface of the object, comparing variations in waveform energy, and thereby localizing an origin of the acoustic emission. The localized origin of the acoustic emission is then displayed.

BRIEF DESCRIPTION OF THE DRAWING

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

The FIGURE is a diagram partially in schematic form, that depicts the apparatus embodying this invention.

DESCRIPTION OF THE PREFERRED EMBODIMENT

Referring to the FIGURE, element 12 generally depicts the surface skin 12 of a patient being examined. At least three sensors 10 are shown adhered to the skin 12 of the patient. Adhesion of the sensors 10 to the skin can be by any known method which will secure the sensors for the duration of expected measurements.

In the embodiment shown, sensors 10 are strain gages, although it should be understood that various alternative sensor devices including accelerometers, hydrophones, microphones, laser velocimeters, and motion detectors may be utilized. Further, the sensors 10 are positionable either in a linear or a planar array as long as three sensors 10 exist on a single axis. Preferably, each sensor in an array is spaced from an adjacent sensor by a distance at least one-half wavelength of the waveform energy being measured. Multiple sensors 10 are necessary to determine the position of the arterial stenoses although for simplicity, only three sensors 10 are shown in the FIGURE.

Each of the plurality of sensors 10 are respectively electrically connected to an analog to digital converter 14, which is in turn connected to a microprocessor 16. The microprocessor 16 is in turn connected to a display device 18 such as a cathode ray tube for displaying results of the processing.

Blood flow through an artery 20 that contains a partial obstruction or occlusion 22 will produce a change in the flow field within the artery from a laminar flow field to a turbulent flow field. Accordingly, wave motion originating at the occlusion is ultimately detected on the surface of the skin 12 by the array of sensors 10.

When an occlusion 22 or obstruction interrupts the flow field within the artery 20, a fluctuating pressure field is created on the artery wall due to the flow becoming turbulent. Within the arteries themselves, the fluctuating pressure field excites breathing waves, and further generates compressional and shear waves in the tissue of the patient. Breathing waves are caused by a fluid structure interaction that propagates in a fluid-filled object having a circular cross-section. In other words, the wave forms propagating from the occlusion within the artery will generate predetermined wave structures as bounded by the circular cross-section of the artery itself, and the breathing waves are detectable at the surface of the skin upon conversion thereof to a shear wave by a wave number conversion process known in the art. By way of reference, shear waves are understood to be equivoluminel waves that propagate in solids.

The compressional and shear waves which are generated and determined on the basis of the wave number conversion propagate to the surface of the skin 12. When the waves interact with the surface of the skin, Raleigh surface waves are also detected. Each of these waves produces a motion in the skin which is detectable using any variety of non-invasive sensors 10, formed in an array as described.

More specifically, wave motion at the surface of the skin causes a displacement in the skin 12 of the patient which in turn causes a change in the resistance of sensors 10. The change in resistance of the sensors 10 is converted by the analog to digital converter 14 and can then be detected and analyzed by the microprocessor 16 and viewed at the display device 18.

In the preferred embodiment of the present invention, known common noise signals are removed from the signals following conversion from an analog to a digital signal. However, it should be understood that reduction of common noise signals including environmental noise, heartbeat, pulse, and breathing can be performed either before or after analog to digital conversion at element 14.

The signals output by each of the analog to digital converters 14 are analyzed by the microprocessor 16 after removing noise to determine if an arterial stenosis or occlusion 22 exists and to determine the location of the stenosis. These determinations are specifically made on the basis of the resulting waveforms detected at the surface of the skin 12 by the sensors 10. A signal with the higher volume indicates a possible arterial stenoses. The stenoses can be localized by solving simultaneous inverse square decay equations for each sensor 10.

Various data of the waveform detected include spectral, directional and intensity measurements of the wave field acquired by the array of sensors 10. Based on these measurements, an assessment of the arterial blockage can be made. Specifically, the spectral intensity level relates to the cross-sectional area of the blockage within the arteries since large blockages produce a higher signal than small blockages. The spectral shape is related to the blockage geometry.

Directional measurements are likewise determined based on the data received from each of the individual sensors 10, and assist in localizing the blockage 22.

As indicated, the plurality of sensors can include accelerometers, hydrophones, microphones, laser velocimeters, strain gages, and motion detectors. The array of sensors can be such that each of the sensors is of the same type, or alternatively, sensors of different types may be mixed in order to detect wave motion or displacement in the form of momentum transfer at the surface of the skin. It is possible for the array of sensors to be linear, two-dimensional or three-dimensional and may be attached to the skin surface at various locations to form the array. Output from the sensors is recorded and processed to determine whether or not the patient has artery disease and the extent of the pathological condition.

Thus, the sensor array utilized in the present invention is a new method for acquiring data applied to the problem of detecting, locating and analyzing energy emissions in three-dimensional objects, and more specifically for the location of artery stenoses in blood vessels. The array detects momentum transfer that exists in the object in the form of wave energy, this detection occurring on the surface of the skin thereby rendering a non-intrusive method.

The present inventors have further discovered that use of the sensor array enhances and localizes energy emanating from an occluded artery and multiple occlusions can be localized using the same array. Further, use of the array provides an improved signal to noise ratio over that of a single sensor. Thus, more precise localization of an occlusion than heretofore known is obtainable.

It should be understood that different sensors have varying frequency responses and positioning characteristics and should be utilized in accordance with their known advantages and features. In other words, microphones may need to be positioned a slight distance away from the skin to receive a signal, whereas accelerometers must be positioned directly on the skin.

This invention has been disclosed in terms of certain embodiments. It will be apparent that many modifications can be made to the disclosed apparatus and method without departing from the invention. For example, known processors, displays, converters and sensors have been utilized, it being understood that the invention resides in the method and apparatus for locating artery stenoses in blood vessels by the use of sensor array technology not previously utilized in the art. Therefore, it is the intent of the appended claims to cover all such variations and modifications as come within the true spirit and scope of this invention.

What is claimed is:

1. A method for detecting arterial blockage in a body containing blood vessels, comprising the steps of:

positioning an array of sensors on a surface of the body;

detecting waveform energy on the body surface by said positioned array of sensors;

identifying a change in waveform energy on the surface of the body by at least one sensor in said array of sensors;

determining at least spectral, directional, and intensity waveform energy characteristics sensed by each sensor in said array of sensors; and locating the arterial blockage from said waveform energy characteristics, wherein said step of positioning includes spacing each sensor in said array from an adjacent sensor by a distance at least one-half wavelength of the waveform energy being measured.

2. The method according to claim 1 wherein the waveform energy detected is vibrational energy having compressional waves, shear waves and Raleigh surface waves.

3. The method according to claim 2 wherein the array of sensors comprises a plurality of sensors selected from the group of vibrational sensors including accelerometers, hydrophones, microphones, laser velocimeters, strain gages, and motion detectors.

4. The method according to claim 3 wherein said array is a linear arrangement of sensors.

5. The method according to claim 3 wherein said array is a two-dimensional arrangement of sensors.

6. The method according to claim 3 wherein said array is a three-dimensional arrangement of sensors.

7. The method according to claim 1 wherein said array is a linear arrangement of sensors.

8. The method according to claim 1 wherein said array is a two-dimensional arrangement of sensors.

9. The method according to claim 1 wherein said array is a three-dimensional arrangement of sensors.

10. A device for detecting arterial stenoses within a body containing blood vessels, comprising:

a sensor array adapted to be positioned on the surface of the body, each sensor in said sensor array detecting waveform energy on a surface of the body and outputting a representative analog signal;

means for converting the analog waveform signal to a digital signal;

a microprocessor unit, responsive to said converted digital signal, for reducing background noise and identifying variations in waveform energy at the surface of the body, comparing variations in waveform energy, and thereby localizing an origin of the arterial blockage; and display means joined to said microprocessor unit for displaying the localized origin of the arterial blockage, wherein each sensor in said array of sensors is spaced from an adjacent sensor by a distance one-half of the wavelength of the waveform energy being measured.

11. The device according to claim 10 wherein the waveform energy detected include compressional waves, shear waves and Raleigh surface waves.

12. The device according to claim 11 wherein the sensors in the array include at least one of accelerometers, hydrophones, microphones, laser velocimeters, strain gages and motion detectors.

13. The device according to claim 12 wherein said array is linear.

14. The device according to claim 12 wherein said array is two-dimensional.

15. The device according to claim 12 wherein said array is three-dimensional.

16. The device according to claim 10 wherein said array is linear.

17. The device according to claim 10 wherein said array is two-dimensional.

18. The device according to claim 10 wherein said array is three-dimensional.

* * * * *